Jan. 15, 1963 A. ASPESLAGH ET AL Plant Pat. 2,220
FICUS PLANT
Filed March 30, 1962
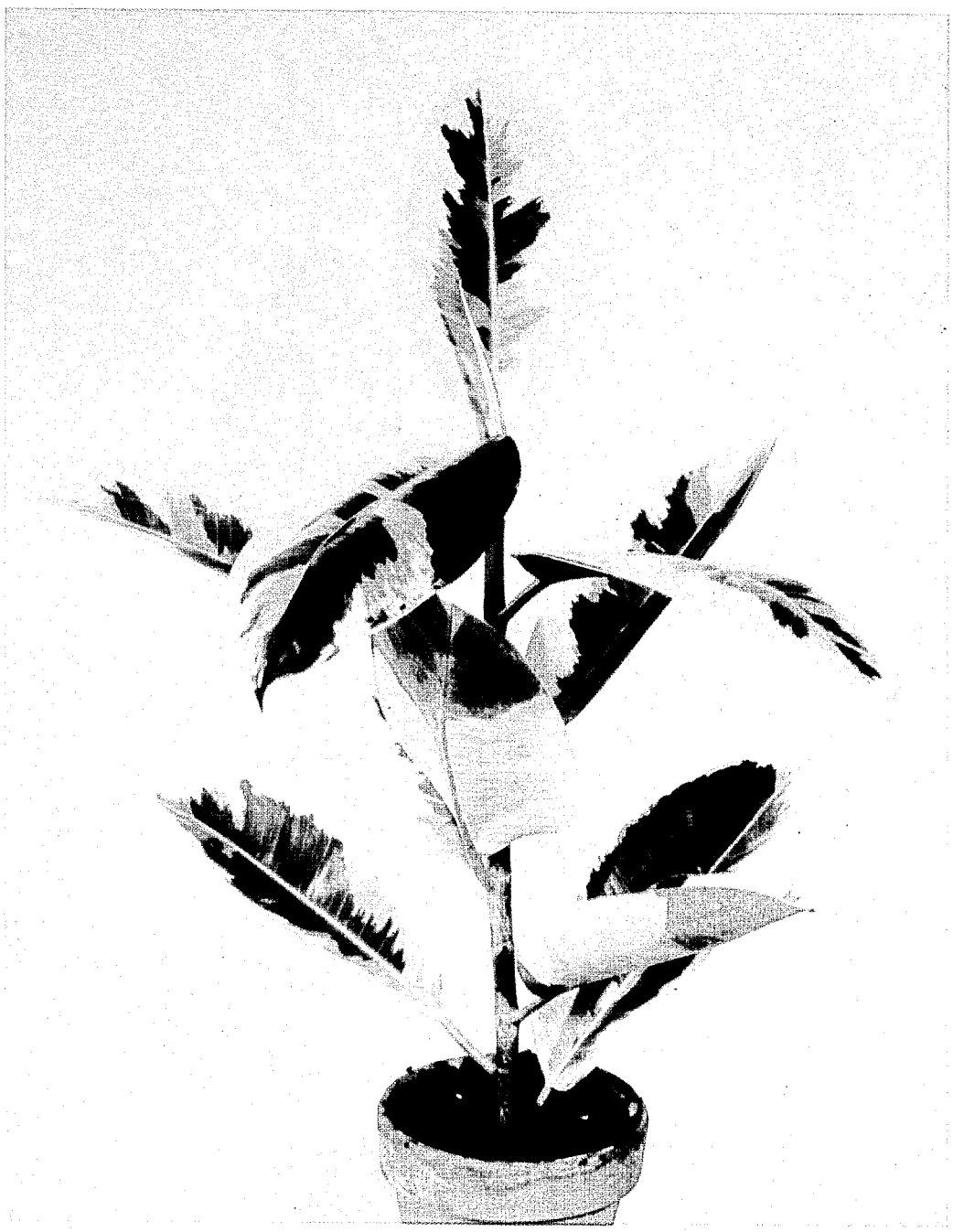
INVENTORS
Albert Aspeslagh and
August van Speybrouck
BY
Robb & Robb
ATTORNEYS United States Patent Office Plant Pat. 2,220
Patented Jan. 15, 1963

2,220
FICUS PLANT

Albert Aspeslagh, Bruges, and August van Speybrouck, Sysele, Belgium, assignors to Horticulture Flandria, Societe Anonyme Assebroek, near Bruges, Belgium, a corporation of Belgium Filed Mar. 30, 1962, Ser. No. 183,985
1 Claim. (Cl. 47—59)

The present invention relates to a new and distinct variety of Ficus plant which originated as a sport of the variety (hort.) *Ficus elastica decora.*

At the time of our discovery of this new sport, our assignee, by whom we were employed, was engaged in growing plants of the variety (hort.) *Ficus elastica decora* in greenhouses on the property of our assigne at Assebroek, near Bruges, Belgium. At that time, the annual production of these plants numbered over one hundred and fifty thousand (150,000). While engaged in taking cuttings from these plants for the purpose of reproducing the same, our attention was directed to one particular plant which exhibited a substantially different appearance from the regular plants of the variety (hort.) *Ficus elastica decora,* as evidenced by its more variegated coloring, and by a definite pink to reddish color on the new leaves of the plant. On closer examination of this particular plant, it was found that it had sported, and accordingly steps were immediately taken to carefully preserve the sport, keep it under close observation, and later on to asexually reproduce the same.

As the result of the foregoing, we have conclusively determined and established that our newly discovered cultivated sport is distinct from the variety (hort.) *Ficus elastica decora,* as well as distinct from all other Ficus varieties of which we are aware, as evidenced by the following unique combination of characteristics which are outstanding in our new variety:

A general appearance and growing habit corresponding to that of the variety (hort.) *Ficus elastica decora,* but with more attractive and distinctive large, glossy leaves which usually are quite variegated in color throughout the entire plant, with the colors ranging through various shades of green, yellow and ivory in general color tonality, said green colors being deepest toward the midrib and being surrounded by various shades of yellow and ivory colors, and substantially all the young leaves having a definite pink to reddish cast throughout on both surfaces which diminishes and usually disappears as the leaves mature.

The nearest approach to our new variety is probably that of U.S. Plant Patent No. 1,519, issued September 18, 1956, but our new variety is clearly differentiated therefrom by its more extensively variegated leaves, with the variegations occurring in all of the leaves of the entire plant, and combined with a marked pink to reddish coloring on all of the young leaves, said latter coloring being completely absent in the previously patented variety aforementioned. Moreover, the coloring of our new variety is more attractive because of the more extensive variegation thereof and the absence of brown spots which tend to give the previously patented variety a "dead" appearance as the leaves mature.

Asexual reproduction of our new variety, as performed by us by both top-cuttings and leaf-cuttings, as carried out in Belgium, shows that the foregoing characteristics and distinctions come true to form and are established and transmitted through succeeding propagations.

The accompanying drawing shows a typical specimen plant of our new Ficus variety as depicted in color as nearly true as it is reasonably possible to make the same in a color illustration of this character.

The following is a detailed description of our new variety, with color terminology in accordance with the Horticultural Colour Chart, edited by the British Colour Council in collaboration with the Royal Horticultural Society, except where general color terms of dictionary significance are obvious:

Parentage: Sport of variety (hort.) *Ficus elastica decora.*

Propagation: Holds its distinguishing characteristics through succeeding propagations by both top-cuttings and leaf-cuttings.

General appearance and growing habit: Corresponds generally to the variety (hort.) *Ficus elastica decora,* particularly with respect to the size and shape of the leaves.

Leaves: Rather thick; leathery; shiny; with parallel nerves extending at an angle to the strongly marked midrib toward the margins; all the leaves show the typical variegation.

*Shape.*—From oval to elliptical.

*Color.*—Center of leaves—irregular variegation of green shades between the nerves, with the color being deeper towards the midrib of each leaf and ranging from Spinach Green, Plate 0960 through Parsley Green, Plate 0962 to Ivy Green, Plate 1060, with lighter variegations ranging from Lavender Green, Plate 000761 to Sung Green, Plate 000658. Edges of leaves—around the green variegation, the edges of the leaves are colored Light Canary Yellow, Plate 2/3 for a depth of from ¼ inch to 2 inches, this color turning to ivory yellow as the leaves mature. Overcast—all new leaves show a very definite pink to reddish color on both surfaces, this coloring spreading over the entire leaf and covering both the green and yellowish areas, and ranging from Shell Pink, Plate 516 through Mandarin Red, Plates 17/2 and 17/3 to Brick Red, Plate 016/3, these latter colorings diminishing and ultimately disappearing as the leaves mature.

Petioles: Color—from pink to scarlet and ultimately turning to greenish red or green.

We claim:

A new and distinct variety of Ficus plant, substantially as hererin shown and described, characterized particularly as to novelty by a general appearance and growing habit corresponding to that of the variety (hort.) *Ficus elastica decora,* but with more attractive and distinctive large, glossy leaves which usually are quite variegated in color throughout the entire plant, with the colors ranging through various shades of green, yellow and ivory in general color tonality, said green colors being deepest toward the midrib and being surrounded by various shades of yellow and ivory colors, and substantially all the young leaves having a definite pink to reddish cast throughout on both surfaces which diminishes and usually disappears as the leaves mature.

No references cited.